(12) United States Patent
DeJuliis

(10) Patent No.: US 9,602,779 B2
(45) Date of Patent: Mar. 21, 2017

(54) SYSTEM FOR PASSENGER MONITORING

(71) Applicant: Christopher DeJuliis, Monongahela, PA (US)

(72) Inventor: Christopher DeJuliis, Monongahela, PA (US)

( * ) Notice: Subject to any disclaimer, the term of this patent is extended or adjusted under 35 U.S.C. 154(b) by 541 days.

(21) Appl. No.: 13/937,869

(22) Filed: Jul. 9, 2013

(65) Prior Publication Data

US 2014/0015971 A1 Jan. 16, 2014

Related U.S. Application Data

(60) Provisional application No. 61/670,009, filed on Jul. 10, 2012.

(51) Int. Cl.
*H04N 7/18* (2006.01)
*A61B 5/00* (2006.01)
*A61B 5/0205* (2006.01)
*B60R 1/00* (2006.01)
(Continued)

(52) U.S. Cl.
CPC ........... *H04N 7/18* (2013.01); *A61B 5/02055* (2013.01); *A61B 5/6893* (2013.01); *B60R 1/00* (2013.01); *H04N 7/181* (2013.01); *H04N 7/183* (2013.01); *A61B 5/1115* (2013.01); *B60R 2011/0017* (2013.01); *B60R 2011/0026* (2013.01); *B60R 2300/8013* (2013.01)

(58) Field of Classification Search
CPC . A61B 5/02055; A61B 5/1115; A61B 5/6893; B60R 1/00; B60R 2011/0017; B60R 2011/0026; B60R 2300/8013; H04N 7/18; H04N 7/181; H04N 7/183

USPC ......................................................... 348/148
See application file for complete search history.

(56) References Cited

U.S. PATENT DOCUMENTS 6,208,256 B1 * 3/2001 Fleming ............... B60K 28/066
   180/271
6,809,643 B1   10/2004 Elrod et al.
(Continued)

FOREIGN PATENT DOCUMENTS

DE  20 2009 008 746 U1  1/2010
DE  10 2010 053 531 A1  6/2012
JP        2011-230529 A  11/2011

OTHER PUBLICATIONS

Partial International Search Report for International Application No. PCT/US2013-049889 dated Jan. 17, 2014.
(Continued)

*Primary Examiner* — Francis G Geroleo
(74) *Attorney, Agent, or Firm* — Moore & Van Allen PLLC; Peter B. Stewart

(57) ABSTRACT

In one aspect, the present invention embraces a system for passenger monitoring. The system typically includes a monitoring device and a monitor positioned in a motor vehicle. The monitoring device typically includes a camera having a field of view directed towards a first passenger location in the motor vehicle. The monitor typically includes a user interface and a processor in communication with the user interface and the monitoring device. The user interface typically includes a visual display. The processor is typically configured to receive images from the camera and display the images on the visual display in near real time.

18 Claims, 11 Drawing Sheets

(51) Int. Cl.
*B60R 11/00* (2006.01)
*A61B 5/11* (2006.01)

(56) References Cited

U.S. PATENT DOCUMENTS

| | | | | | |
|---|---|---|---|---|---|
| 7,463,161 | B2* | 12/2008 | Griffin | | B60N 2/002 |
| | | | | | 180/271 |
| 8,179,274 | B2* | 5/2012 | Rork | | B60N 2/002 |
| | | | | | 297/216.11 |
| 8,643,493 | B1* | 2/2014 | Klitenick | | G08B 21/24 |
| | | | | | 340/457 |
| 2003/0098909 | A1* | 5/2003 | Fritzsche | | B60R 1/00 |
| | | | | | 348/148 |
| 2004/0090525 | A1* | 5/2004 | Eichmann | | B60R 1/00 |
| | | | | | 348/148 |
| 2005/0054935 | A1* | 3/2005 | Rice | | A61B 5/0059 |
| | | | | | 600/473 |
| 2005/0200465 | A1* | 9/2005 | Fabors | | B60Q 1/50 |
| | | | | | 340/457 |
| 2009/0134984 | A1* | 5/2009 | Chen | | B60Q 1/268 |
| | | | | | 340/425.5 |
| 2009/0174774 | A1 | 7/2009 | Kinsley | | |
| 2009/0284598 | A1* | 11/2009 | Busch | | B60R 1/00 |
| | | | | | 348/148 |
| 2010/0060733 | A1* | 3/2010 | Lakshmanan | | H04N 7/185 |
| | | | | | 348/143 |
| 2010/0090836 | A1* | 4/2010 | Trummer | | B60N 2/2812 |
| | | | | | 340/573.1 |
| 2010/0109878 | A1* | 5/2010 | Desrosiers | | H04N 7/185 |
| | | | | | 340/573.4 |
| 2011/0039524 | A1* | 2/2011 | Gross | | G08C 17/00 |
| | | | | | 455/414.1 |
| 2013/0049955 | A1* | 2/2013 | Hoover | | B60N 2/28 |
| | | | | | 340/539.11 |
| 2013/0157647 | A1* | 6/2013 | Kolodziej | | H04M 1/72522 |
| | | | | | 455/419 |
| 2013/0303106 | A1* | 11/2013 | Martin | | H04W 4/12 |
| | | | | | 455/404.2 |
| 2014/0118548 | A1* | 5/2014 | Veneziano | | H04N 7/183 |
| | | | | | 348/148 |
| 2015/0085116 | A1* | 3/2015 | Graumann | | B60R 1/025 |
| | | | | | 348/148 |

OTHER PUBLICATIONS

International Search Report and Written Opinion for International Application No. PCT/US2013/049889 dated Mar. 18, 2014.
International Preliminary Report on Patentability and Written Opinion dated Jan. 13, 2015.

* cited by examiner

SYSTEM FOR PASSENGER MONITORING

CROSS-REFERENCE TO RELATED APPLICATION

This application claims the benefit of U.S. patent application Ser. No. 61/670,009 for a "System for Passenger Monitoring" (filed Jul. 10, 2012), which is hereby incorporated by reference in its entirety.

BACKGROUND

Traditionally in order to monitor a rear view setting, such as the back seat of a car, the driver must continuously turn around to look behind themselves. This involves the driver taking their eyes off the road and not being attentive for some period of time. To this extent, it only takes a split second for a fatality to occur while the driver is not paying attention to the road. Thus, the continuous action of turning around while operating a motor vehicle can serve to be both dangerous to the driver, other passengers in the car, and other vehicles on the road. Often people still choose to place themselves in danger because of a more demanding sense to constantly monitor an infant or other young children in the back seat of the car to ensure their safety and comfort. However, by not placing equal emphasis on monitoring the road at all times, the driver is placing the child's safety, as well as their own safety, at risk. Furthermore, in some instances the child's car seat may be facing the rear of the vehicle. In such an instance, when turning completely around the driver may still only have a skewed view of the child.

SUMMARY

In one aspect, the present invention embraces a system for passenger monitoring. The system typically includes a monitoring device and a monitor positioned in a motor vehicle. The monitoring device typically includes a camera having a field of view directed towards a first passenger location in the motor vehicle. The monitor typically includes a user interface and a processor in communication with the user interface and the monitoring device. The user interface typically includes a visual display. The processor is typically configured to receive images from the camera and display the images on the visual display in near real time. The monitor is typically positioned in the motor vehicle to that an operator location in the motor vehicle is within a field of view of the visual display.

In one embodiment, a system for passenger monitoring in accordance with the present invention includes a monitoring device positioned in a motor vehicle and that includes a first camera having a field of view directed towards a first passenger location in the motor vehicle. The system also typically includes a mobile device that includes a user interface, a communications system, a motion sensor, and a processor in communication with the user interface, the communications system, the motion sensor, and the first monitoring device. The processor is typically configured to operate a passenger monitoring application that is configured to (i) receive images from the first camera and display the images on the visual display in near real time, (ii) detect motion using the motion sensor, and (iii) in response to a predetermined amount of detected motion, disable any telephone and/or text-messaging functionality of the communications system.

BRIEF DESCRIPTION OF THE DRAWINGS

Figure 1:
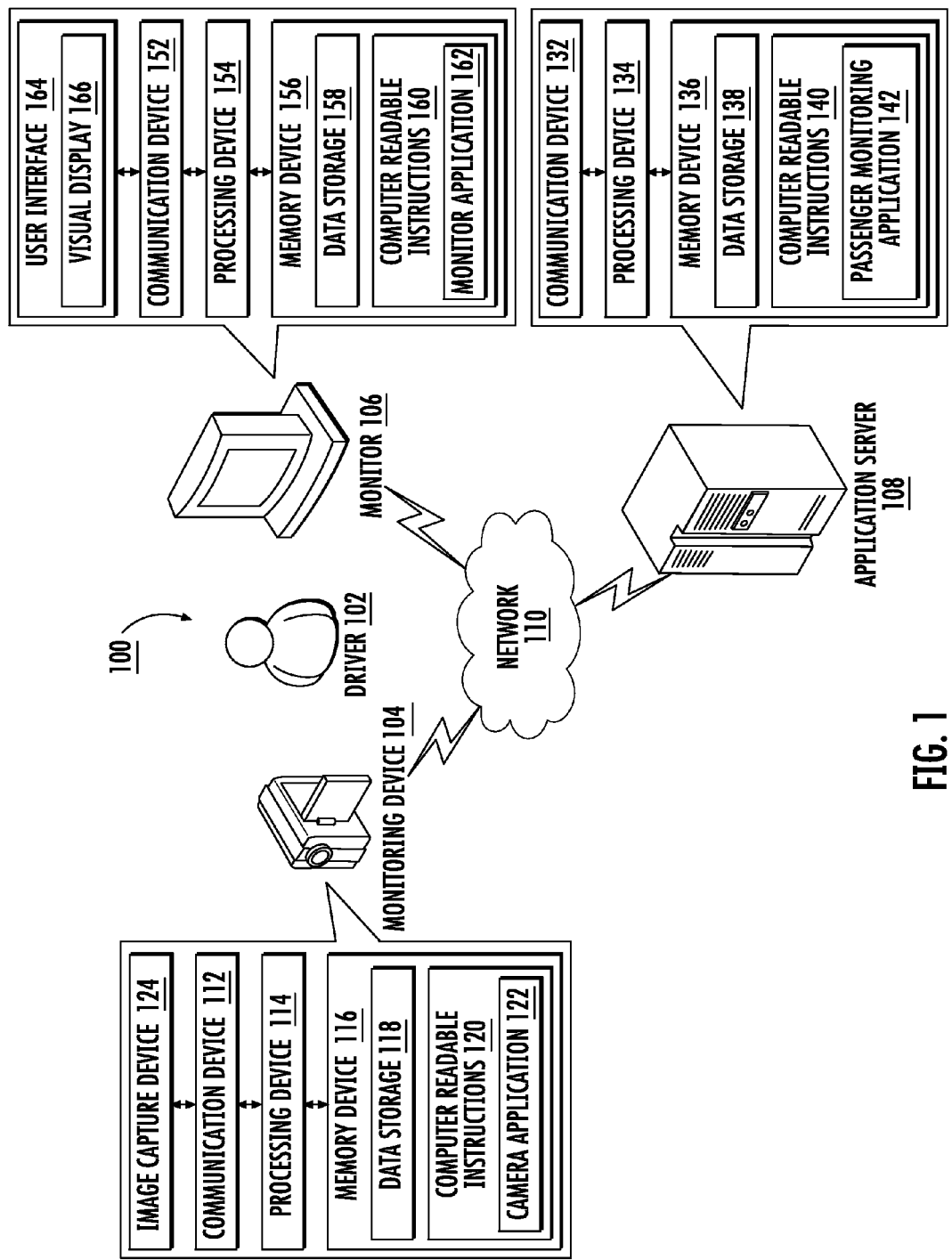
Figure 2:
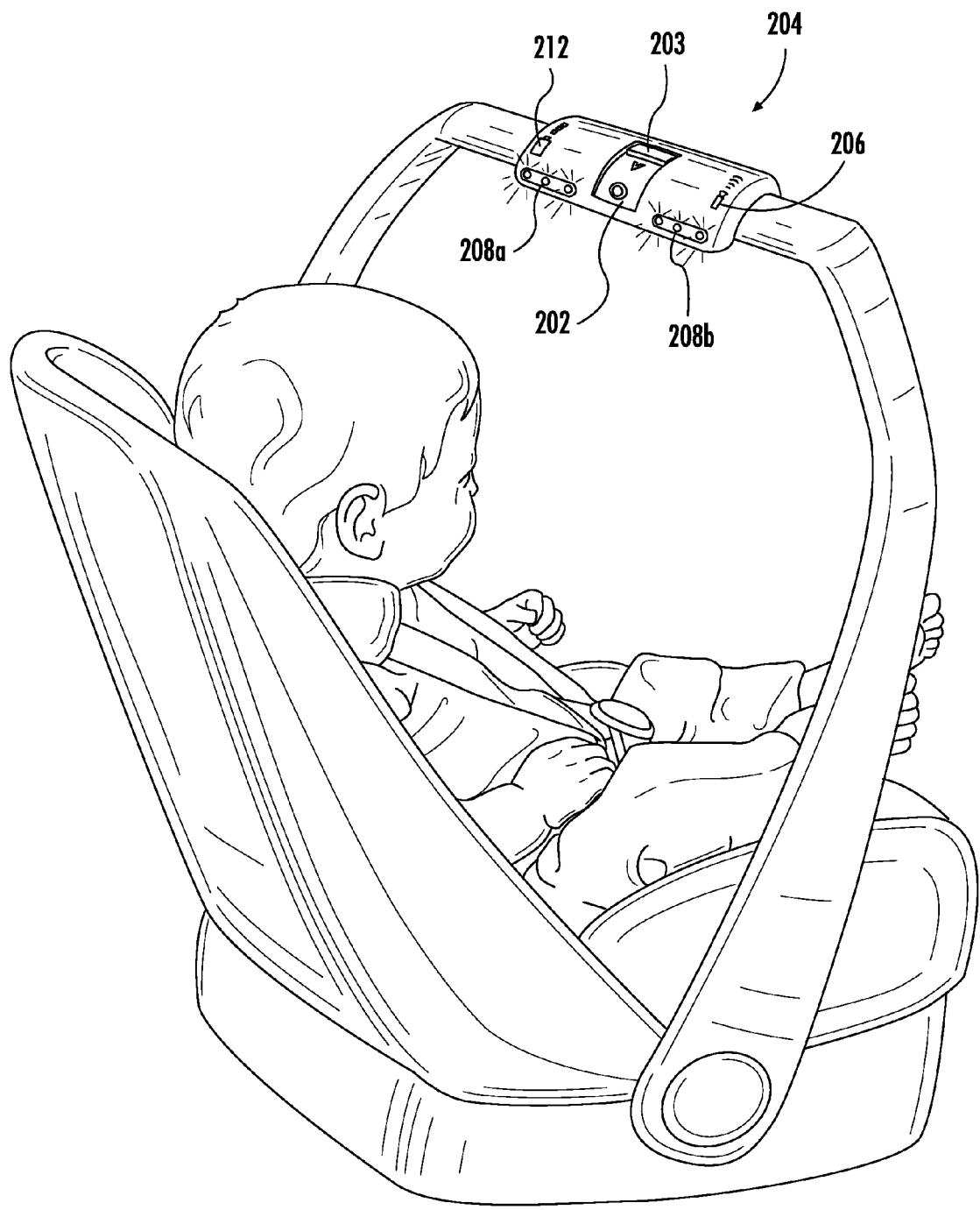
Figure 3A:
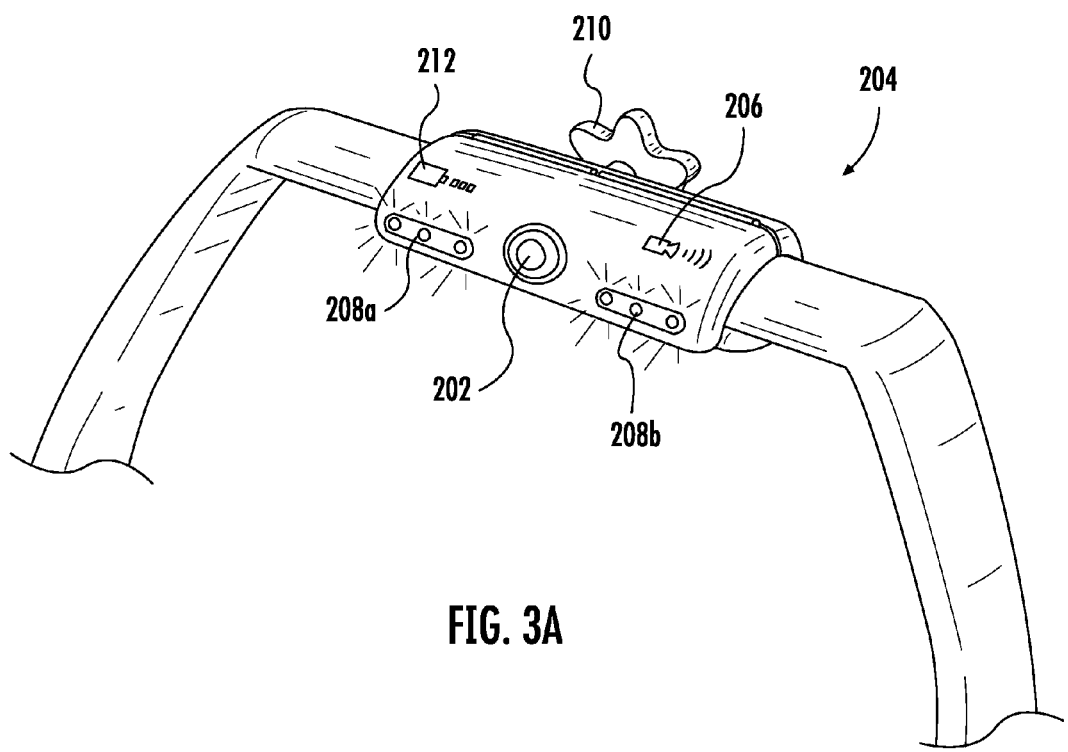
Figure 3B:
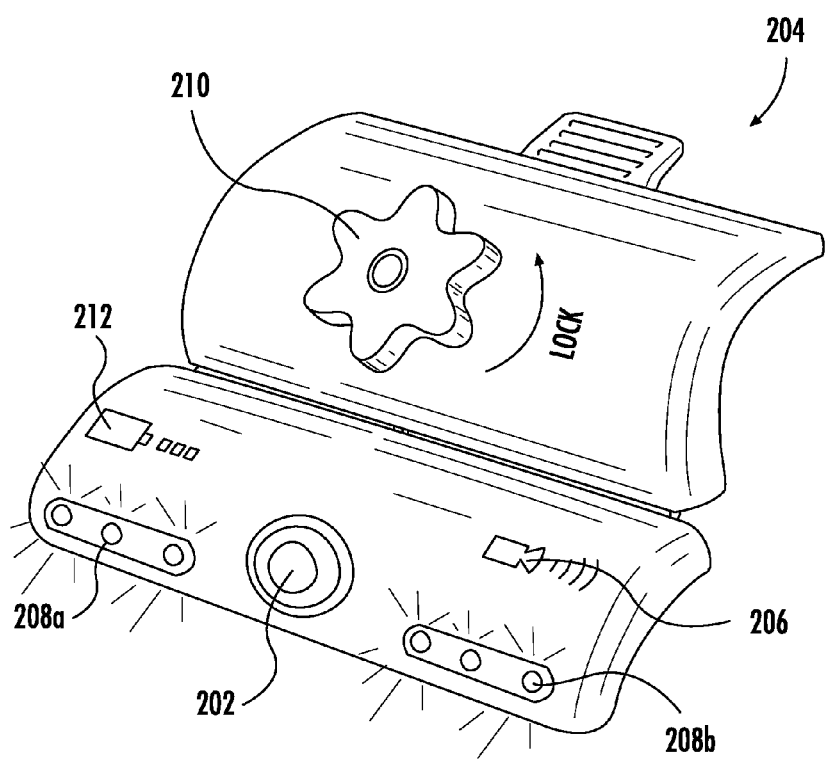
Figure 4:
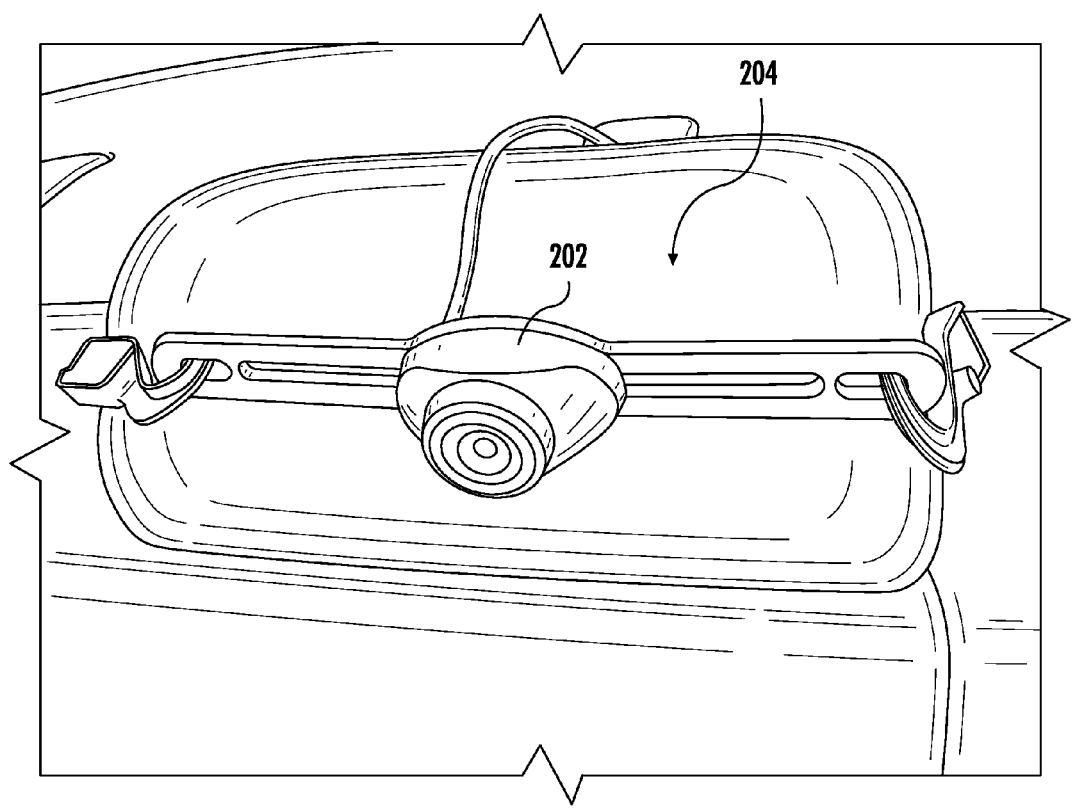
Figure 5:
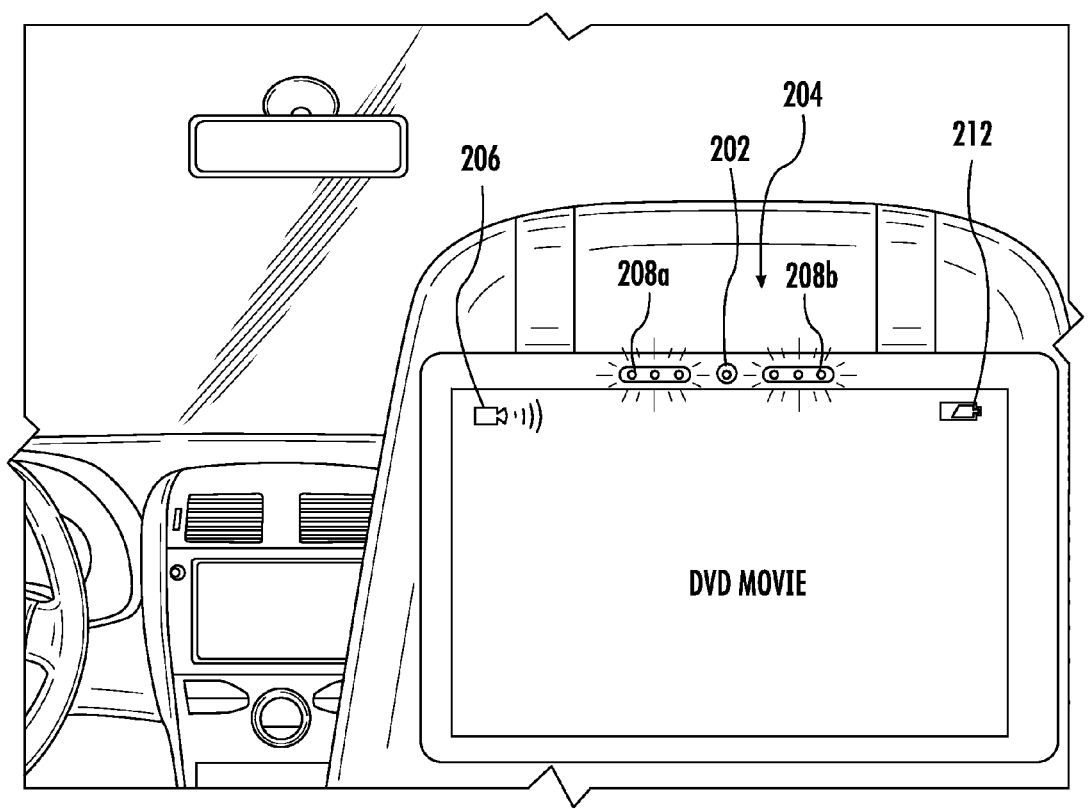
Figure 6:
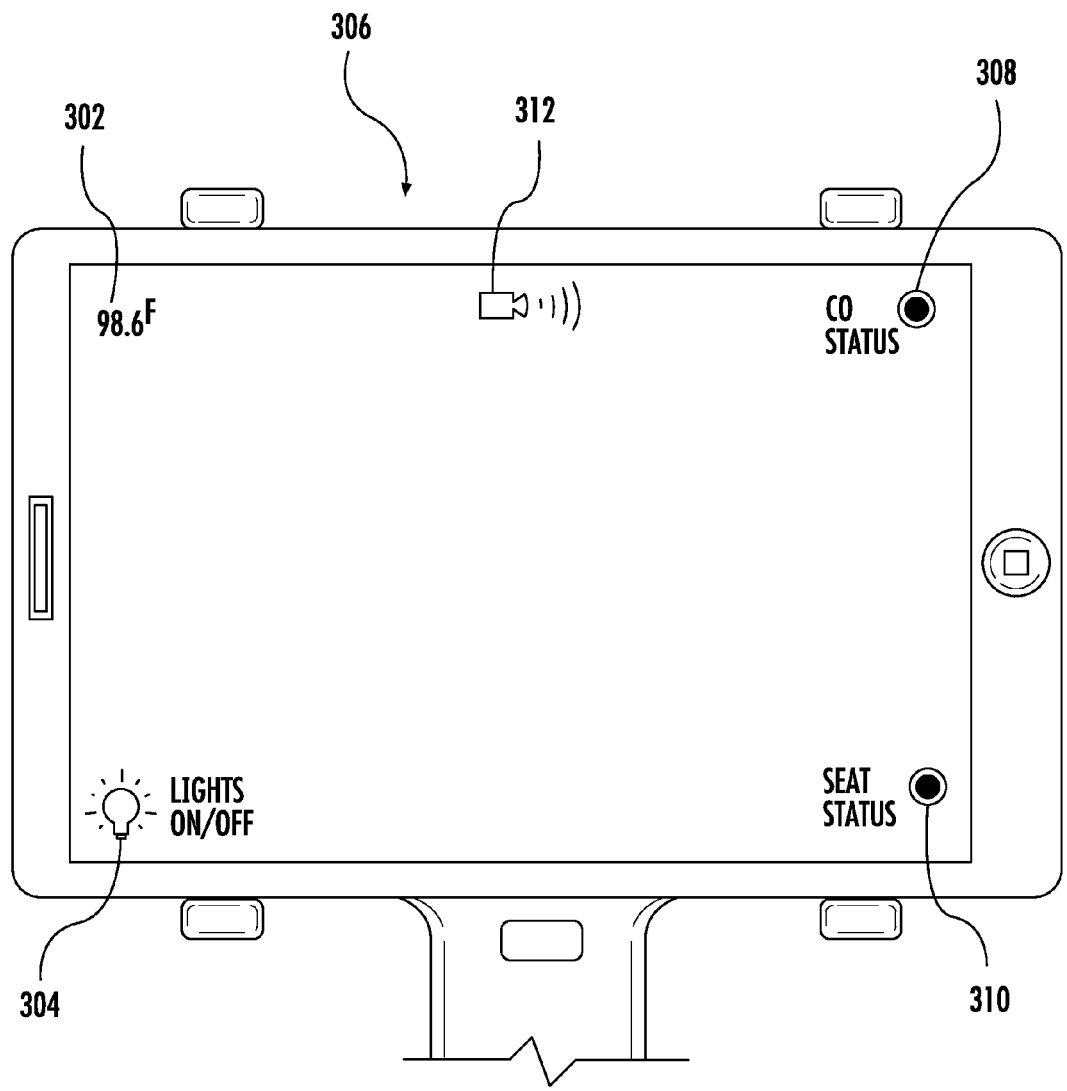
Figure 7:
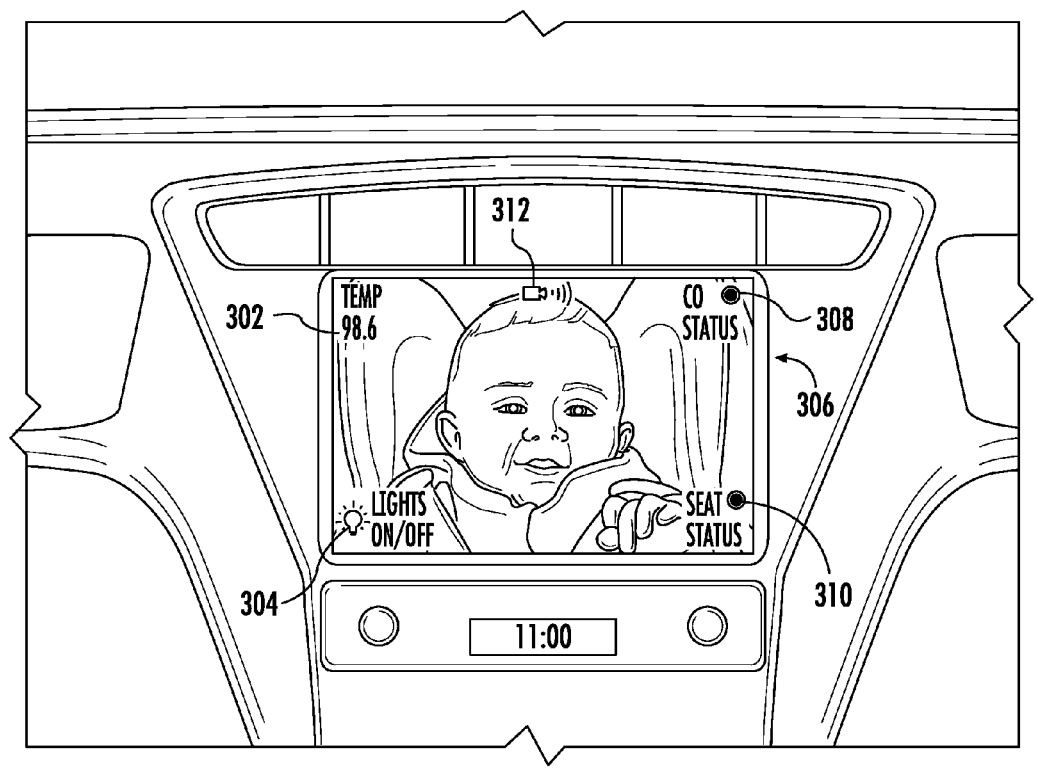
Figure 8:
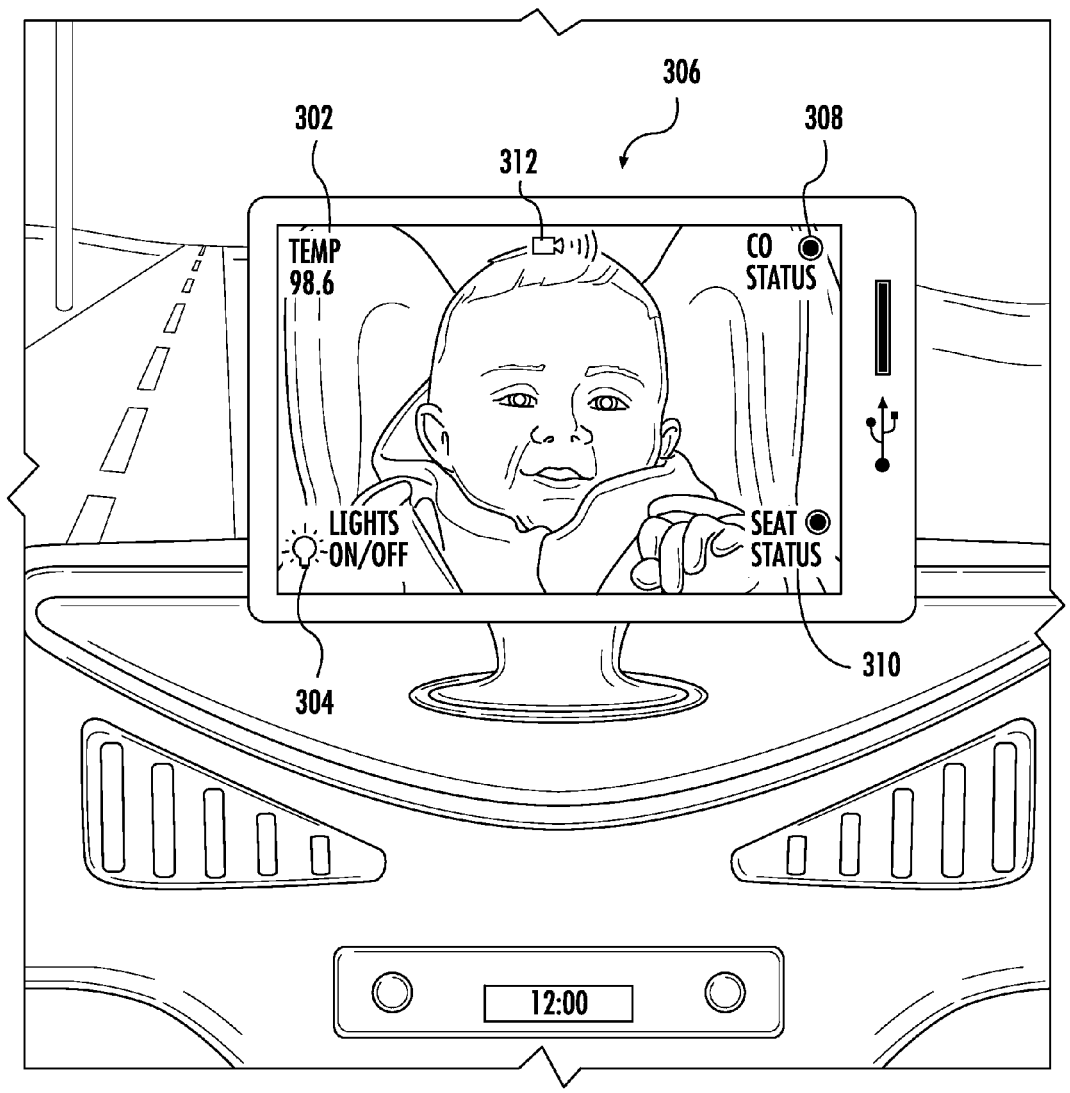
Figure 9A:
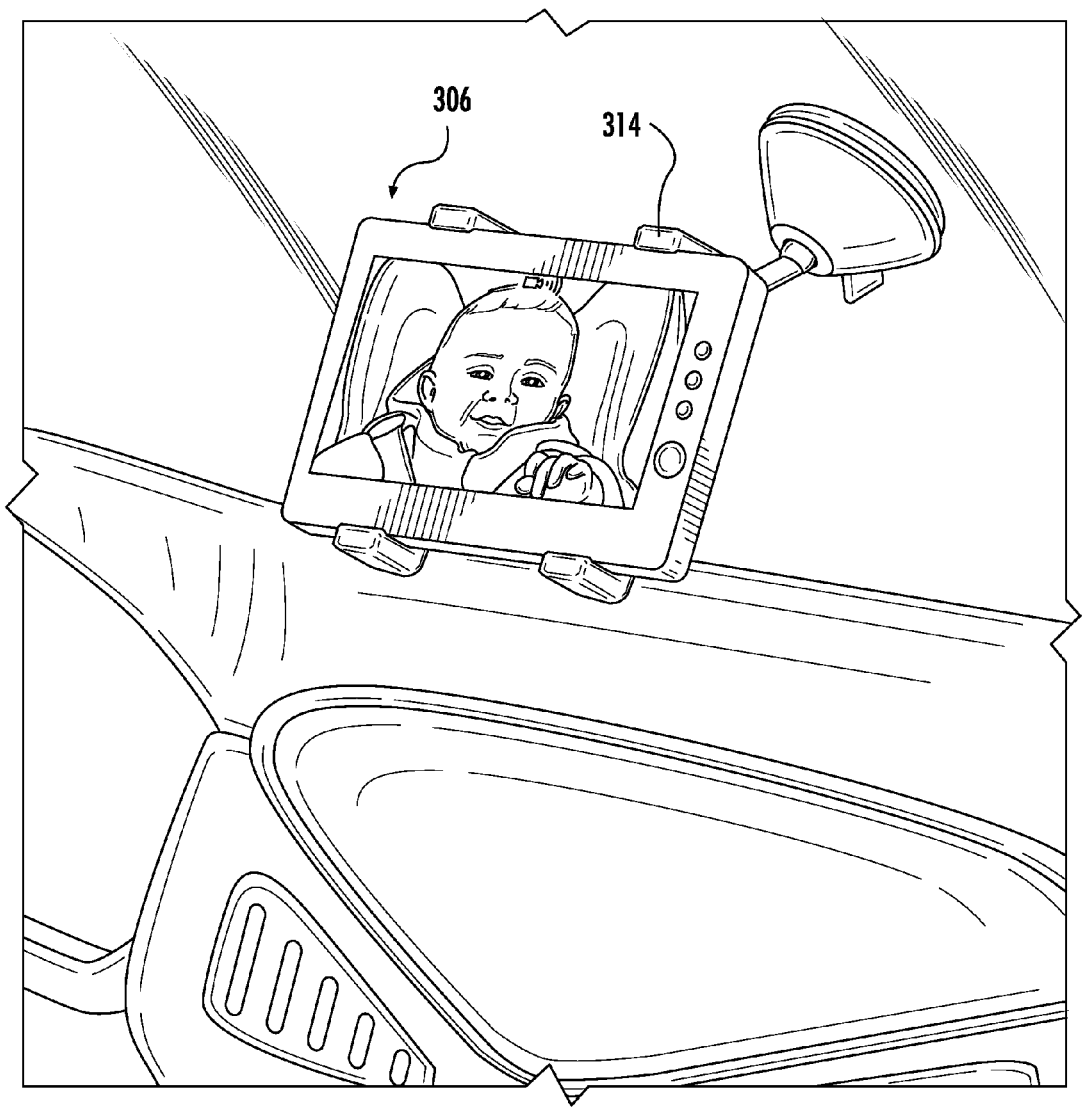
Figure 9B:
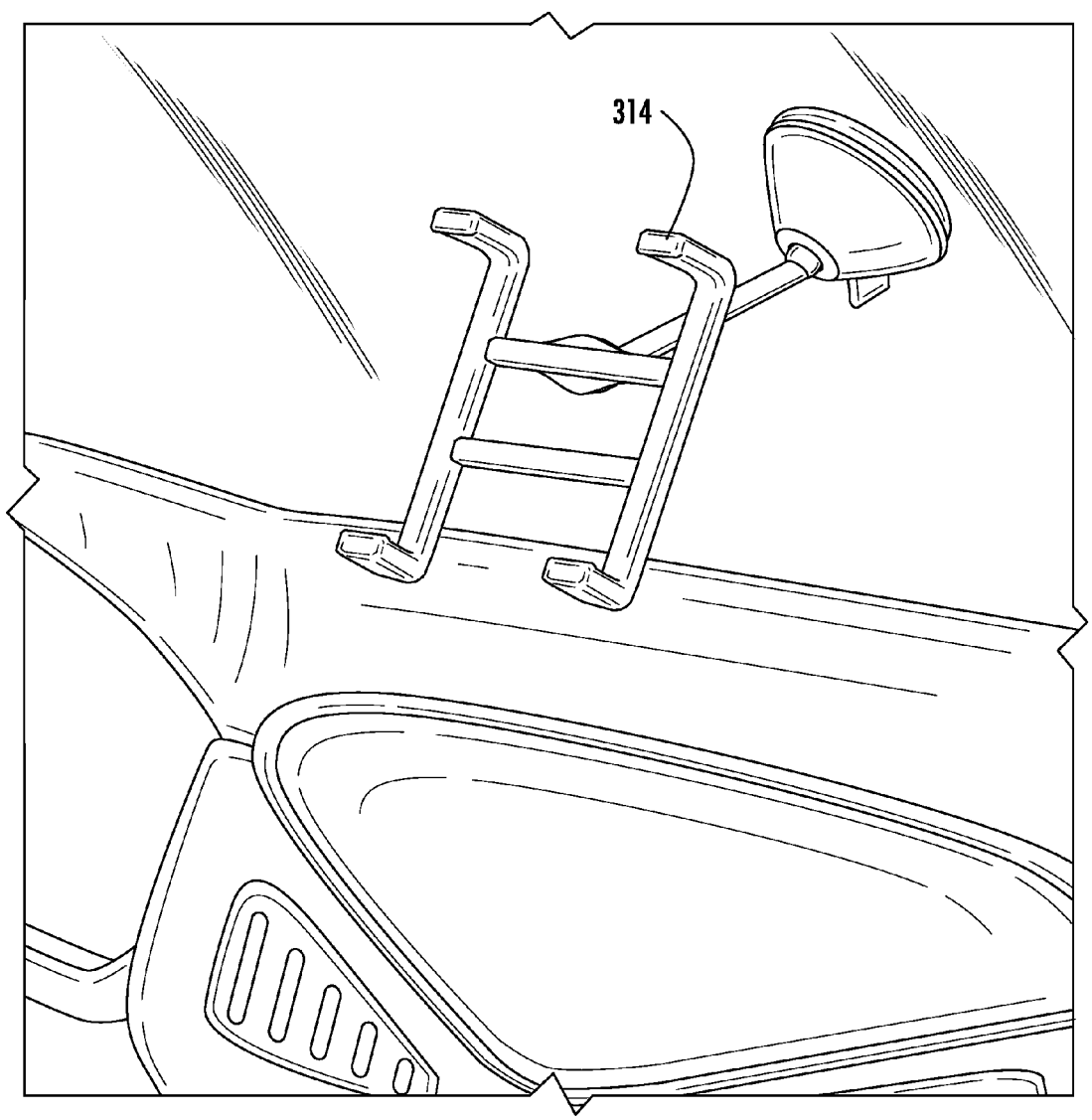
Figure 10:
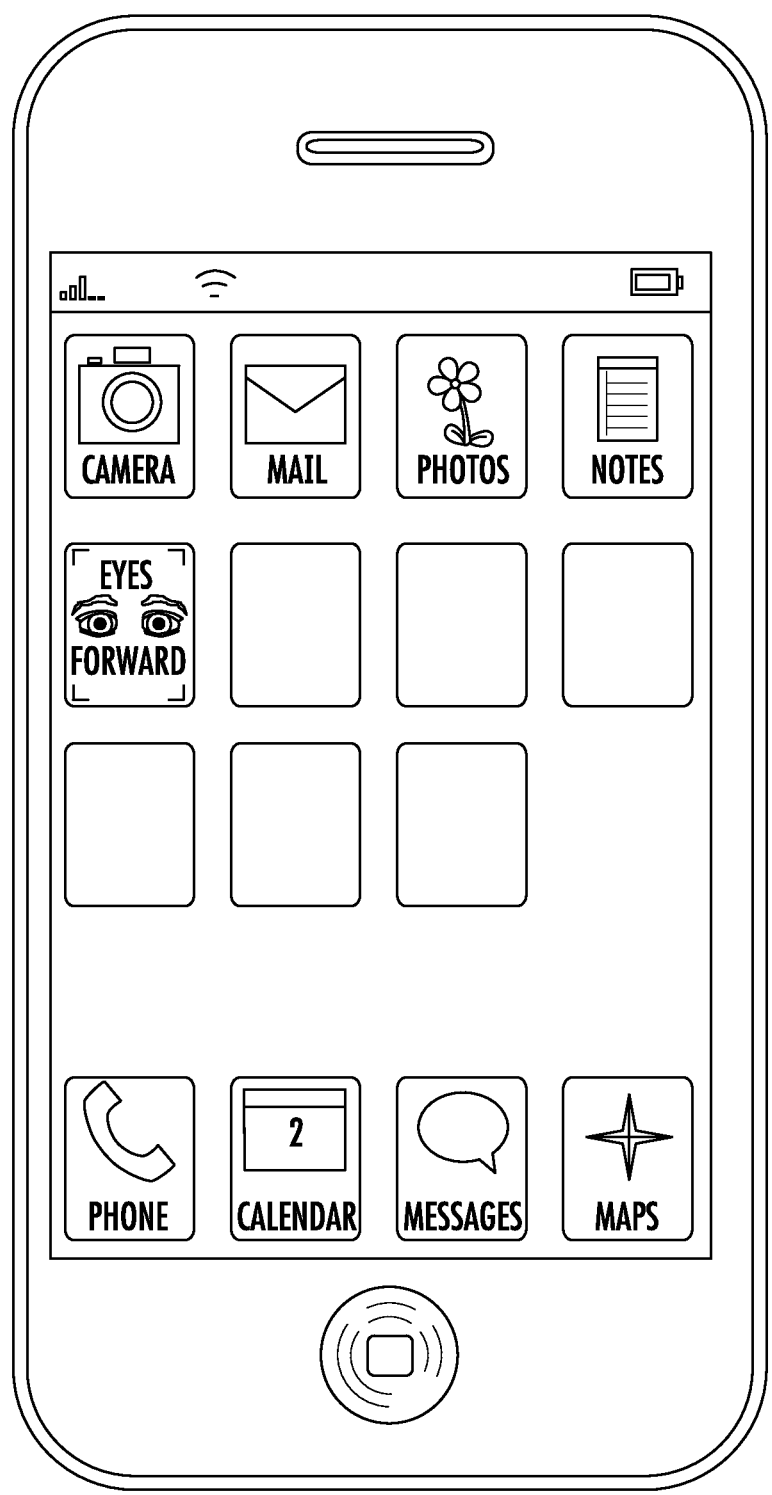

Having thus described embodiments of the invention in general terms, reference will now be made to the accompanying drawings, which are not necessarily drawn to scale, and wherein:

FIG. 1 provides a diagram illustrating a system for passenger monitoring in accordance with one embodiment of the present invention;

FIG. 2 depicts a monitoring device integrated with a child safety seat or car seat handle in accordance with one embodiment of the present invention;

FIG. 3A depicts a monitoring device retrofitted to a child safety seat or car seat handle in accordance with one embodiment of the present invention;

FIG. 3B depicts a monitoring device that can be retrofitted to a child safety seat in accordance with one embodiment of the present invention;

FIG. 4 depicts a monitoring device retrofitted to a car seat headrest in accordance with one embodiment of the present invention;

FIG. 5 depicts a monitoring device retrofitted to a car seat headrest in accordance with another embodiment of the present invention;

FIG. 6 depicts a mobile device being used as a monitor in accordance with one embodiment of the present invention;

FIG. 7 depicts an integrated monitor in accordance with one embodiment of the present invention;

FIG. 8 depicts a monitor being mounted on the dashboard of a motor vehicle in accordance with one embodiment of the present invention;

FIG. 9A depict a monitor being mounted to the front window of a motor vehicle in accordance with one embodiment of the present invention;

FIG. 9B depicts a window mount unit for mounting a monitor in accordance with one embodiment of the present invention;

FIG. 10 depicts a mobile application interface on a mobile device in accordance with one embodiment of the present invention.

DETAILED DESCRIPTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. In the following description, for purposes of explanation, numerous specific details are set forth in order to provide a thorough understanding of one or more embodiments. It may be evident; however, that such embodiment(s) may be practiced without these specific details. Like numbers refer to like elements throughout. Where possible, any terms expressed in the singular form herein are meant to also include the plural form and vice versa, unless explicitly stated otherwise. As used herein a "motor vehicle" typically refers to automobiles, trucks, and buses. That said, other vehicles having room for an operator and at least one passenger, such as boats and airplanes are within the scope of the term "motor vehicle." As used herein a "driver" refers to an individual operating a motor vehicle. Furthermore, as used herein a "passenger" refers to one or more occupants located in the rear of a motor vehicle. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on." Like numbers refer to like elements throughout.

Various embodiments or features will be presented in terms of systems that may include a number of devices, components, modules, and the like. It is to be understood and appreciated that the various systems may include additional devices, components, modules, etc. and/or may not include all of the devices, components, modules etc. discussed in connection with the figures. A combination of these approaches may also be used.

Embodiments of the present invention are described below with reference to flowchart illustrations and/or block diagrams of methods, apparatus (systems), and computer program products. It may be understood that each block of the flowchart illustrations and/or block diagrams, and/or combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create mechanisms for implementing the functions/acts specified in the flowchart and/or block diagram block or blocks.

The steps and/or actions of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some embodiments, the processor and the storage medium may reside in an Application Specific Integrated Circuit (ASIC). In the alternative, the processor and the storage medium may reside as discrete components in a computing device. Additionally, in some embodiments, the events and/or actions of a method or algorithm may reside as one or any combination or set of codes and/or instructions on a machine-readable medium and/or computer-readable medium, which may be incorporated into a computer program product.

In one or more embodiments, the functions described may be implemented in hardware, software, firmware, or any combination thereof. If implemented in software, the functions may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or data structures, and that can be accessed by a computer. Also, any connection may be termed a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. "Disk" and "disc", as used herein, include compact disc (CD), laser disc, optical disc, digital versatile disc (DVD), floppy disk and blu-ray disc where disks usually reproduce data magnetically, while discs usually reproduce data optically with lasers. Combinations of the above should also be included within the scope of computer-readable media.

Thus, methods, systems, computer programs and the like are herein disclosed that provide for a system for passenger monitoring.

FIG. 1 provides a system for passenger monitoring 100, in accordance with one aspect of the present invention. The system for passenger monitoring 100 typically includes one or more monitoring devices 104 in communication (e.g., via a network 110) with one or more monitors 106. The monitoring device 104 typically provides near-real-time images of a passenger within a motor vehicle for display on the monitor 106. Accordingly, a driver 102 (e.g., an operator) of a motor vehicle can monitor passengers (e.g., back seat passengers) via the monitor 106 while the motor vehicle is in motion.

The network 110 may be a global area network (GAN), such as the Internet, a wide area network (WAN), a local area network (LAN), or any other type of network or combination of networks. The network 110 may provide for wireline, wireless, or a combination wireline and wireless communication (e.g., using IP based connectivity) between devices on the network.

As illustrated in FIG. 1, an application server 108 may be operatively coupled, via the network 110 to the monitoring device 104, and to the monitor 106. The application server 108, monitoring device 104 and monitor 106 may all have upgradable firmware. The application server 108 may be configured to send information to and receive information from the monitoring device 104 and the monitor 106 to facilitate passenger monitoring.

As illustrated in FIG. 1, the application server 108 typically includes a communication device 132, a processing device 134, and a memory device 136. As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may include functionality to operate one or more software programs based on computer-readable instructions thereof, which may be stored in a memory device.

The processing device 134 is typically operatively coupled to the communication device 132 and the memory device 136. The processing device 134 uses the communication device 132 to communicate with the network 110 and other devices on the network 110, such as, but not limited to the monitoring device 104 and the monitor 106. As such, the communication device 132 generally includes a modem, server, or other device for communicating with other devices on the network 110.

As further illustrated in FIG. 1, the application server 108 typically includes computer-readable instructions 140 stored in the memory device 136, which in one embodiment includes the computer-readable instructions 140 of a passenger monitoring application 142. In some embodiments, the memory device 136 includes data storage 138 for storing data related to passenger monitoring including but not limited to data created and/or used by the passenger monitoring application 142 or the driver 102 passenger monitoring preferences. The data storage 138 may also store all video files of previous passenger monitoring instances.

In one embodiment, the passenger monitoring application 142 allows the driver 102 to interact with the system. The passenger monitoring application 142 may allow a driver 102 to store preferences for each monitoring instance. The passenger monitoring application 142 typically allows the monitor 106 to receive and display real-time video feed from the monitoring device 104. Both sending and receiving real-time video images may be performed by a using a graphical user interface (GUI) provided by the application 142 via a network 110 to the monitor 106.

In some embodiments, the passenger monitoring application 142 allows the driver 102 to communicate, via the monitor 106, to indicate passenger monitoring preferences that the driver 102 may wish to store or adjust. This communication may be in the form of text communications, voice communications, or the like. Typically, passenger monitoring preferences that the driver 102 may wish to use on a recurring basis may be provided by the driver 102 using the monitor 106 as an interface to store the passenger monitoring preferences in the application server 108. The passenger monitoring application 142 may also receive a real-time request to adjust passenger monitoring settings while video images are currently being captured and streamed by the monitoring device 104.

FIG. 1 illustrates only one example of the system for passenger monitoring 100, and it will be appreciated that in other embodiments one or more of the systems, devices, or servers may be combined into a single system, device, or server, or be made up of multiple systems, devices, or servers. In this regard, it is within the scope of the present invention for the monitoring device 104 to communicate directly with the monitor 106 (e.g., via the network 110) without the need for the intermediary application server 108. For example, the monitoring device and the monitor 106 may communicate directly via short range wireless communications.

Indeed, any sufficient way of communicating between the monitoring device 104 and the monitor 106 is within the scope of the present invention.

The monitoring device 104 may be any device capable of capturing images (e.g., video images). For example, the monitoring device 104 may be a video camera or a mobile device that is cable of capturing images. A "mobile device" may be any mobile communication device, such as a cellular telecommunications device (e.g., a cell phone or mobile phone), personal digital assistant (PDA), a mobile Internet accessing device, or other mobile device including, but not limited to portable digital assistants (PDAs), pagers, mobile televisions, gaming devices, laptop computers, cameras, video recorders, audio/video player, radio, GPS devices, any combination of the aforementioned, or the like. Although a single monitoring device 104 is depicted in FIG. 1, the system for passenger monitoring 100 may contain numerous monitoring devices 104.

As depicted in FIG. 1, the monitoring device 104 typically includes a communication device 112, a processing device 114, a memory device 116, and one or more image capturing devices 124. The processing device 114 is operatively coupled to the communication device 112 and the memory device 116. The processing device 114 uses the communication device 112 to communicate with the network 110 and other devices on the network 110, such as, but not limited to, the monitor 106 and/or the application server 108. As such, the communication device 112 generally includes a modem or other device (e.g., a built-in antenna) for communicating with other devices on the network 110.

As further illustrated in FIG. 1, the monitoring device 104 typically includes computer-readable instructions 120 stored in the memory device 116, which in one embodiment includes the computer-readable instructions 120 of a camera application 122.

The image capturing device 124 may be any device that is capable of capturing images. Typically, the image capturing device 124 is a camera capable of capturing live video images. The monitoring device 104 is typically positioned within a motor vehicle so that the image capturing device's field of view is directed towards a passenger location (e.g., a seat or other place where a passenger may be located, such as a child safety seat) within the vehicle.

In one embodiment, the image capturing device 124 may be a camera with a high quality lens such that it is capable of capturing High-Definition Videos. The camera lens may be adjusted to variable sizes in order to adjust the degree of light and image quality in the monitored image videos. In one embodiment, the camera may have a light adjusting lens such that the lens is self-adjusted depending on the current lighting settings. The camera may also include a plurality of video pixels to render clear images of the monitored passenger(s) and high video resolution quality. In one embodiment, the camera may be a high-quality digital video camcorder that offers as much as 410,000 or more pixels per charge-coupled device (hereinafter, "CCD"). The image capturing device 124 may have image stabilization such that video images are kept stable while being captured in a motor vehicle that is in motion. In one embodiment, the image capturing device 124 may have optical image stabilization such that there is no loss in image quality while capturing images in a moving motor vehicle. The image capturing device 124 may have a recording option such that monitored video files are saved. In one embodiment, the video files may be saved to a mobile device. In another embodiment, the video files may be saved to the application server 108.

The image capturing device 124 may also have a plurality of zoom options. In one embodiment, the image capturing device 124 may have optical zoom capabilities. In another embodiment, the image capturing device 124 may have digital zoom capabilities. The image capturing device 124 may also have facial recognition options. In one embodiment, the facial recognition options may be used for the image capturing device 124 to automatically adjust both the focus and the exposure to capture the best image possible. In another embodiment, the facial recognition options may be used to detect a particular passenger and adjust the passenger monitoring settings based at least partially upon the passenger that was detected. The image capturing device 124 may also have facial coloring technology. In such an embodiment, a user may capture a still phone of a passenger in normal conditions such that when the image is analyzed while the passenger is being monitored in a real-time setting any significant changes in the passengers color may be detected. In one embodiment, a change in passenger color will result in the driver 102 being notified that there is a potential issue with the monitored passenger.

In one embodiment, the monitoring device may include a plurality of image capturing devices. In this regard, the monitoring device may have a master and/or slave option for additional camera integration. As such, one image capturing device (e.g., camera) may server as the primary image capturing device for the monitoring device 104. The monitoring device may further include one or more slave image capturing devices that interface with a master image capturing device. The one or more slave image capturing devices may be connected to the master image capturing device using a pairing technology (e.g., using short range wireless communication). In one embodiment, the multiple image capturing devices may capture multiple views of a monitored passenger. In another embodiment, the multiple image capturing devices may capture images of multiple monitored passengers.

The monitoring device 104 may also include a camera link status indicator that indicates the link status between the camera monitoring device 104 and the monitor 106.

The monitoring device 104 may include one or more options for powering the monitoring device 104. As such, the monitoring device 104 may include a battery life indicator that reflect the battery life of one or more power sources. In one embodiment, the monitoring device 104 may have an independent rechargeable battery. In another embodiment, the monitoring device 104 may be charges using a solar power charging option. In yet another embodiment, the monitoring device 104 may have an independent USB power supply. In a further embodiment, the monitoring device 104 may have an independent USB charger. It should be noted that the monitoring device 104 may use any combination of one or more independent rechargeable batteries, solar power option(s), independent USB power supplies, and/or independent USB chargers as a source of power. It should be additionally noted that the monitoring device 104 may also be powered by other means of power not listed herein.

In one embodiment, the monitoring device 104 may include a sensor for detecting low lighting conditions. The monitoring device 104 may further include one or more illumination devices (e.g., white LED lights) for providing additional illumination (e.g., additional illumination of the image capturing device's field of view) during low lighting conditions. In this regard, the monitoring device 104 may be configured (e.g., the processing device 114 may be configured) to engage the illumination devices once the sensor detects low lighting conditions. The monitoring device 104 may be further configured to disengage the illumination devices once sufficient lighting conditions have returned.

The monitoring device 104 may include a carbon-monoxide sensor for detecting the level of carbon monoxide in the motor vehicle. The monitoring device 104 may also include a temperature sensor for detecting the temperature in the motor vehicle.

The monitoring device 104 may include audio options to allow for sound recording. In one embodiment, the monitoring device 104 may have a built-in microphone to allow for quality sound recording. In another embodiment, the monitoring device 104 may include a microphone connector. In such an embodiment, the monitoring device 104 may be compatible with any external microphone such that the external microphone is capable of being connected to the monitoring device 104 and transferring monitored sounds to the monitor 106. In one embodiment, the monitoring device 104 may have a standard mini-jack connector for an external microphone. In another embodiment, the monitoring device 104 may have a 3-pin XLR audio connector for an external microphone.

The monitoring device 104 may also include and/or be connected to a sensing seat pad. The sensing seat pad may be integrated with the camera system of the monitoring device 104 to send notifications to the monitor 106. In an embodiment where the monitored passenger is an infant and/or child the sensing seat pad may be positioned in a child safety seat to indicate the child's temperature, heart rate, and whether there is moisture in the child safety seat (e.g., to determine whether or not the child has a wet and/or dirty diaper). This feature may be advantageous as the driver 102 may be notified of such conditions so they are able to safely pull over and attend to the infant and/or child as needed.

In one embodiment, the monitoring device 104 may also include and/or be connected to a seat status sensor. Typically, the seat status sensor is attached to a child safety seat and configured to detect whether a passenger is secured within the child safety seat.

In one embodiment, the monitoring device may be a monitoring device 204 that is integrated with a child safety seat (e.g., an infant safety seat) as depicted in FIG. 2. Such an embodiment may be particularly advantageous in instances where an infant's car seat is positioned to face the rear of the motor vehicle.

As illustrated in FIG. 2, in one embodiment, the monitoring device 204 may be integrated with the handle of the car seat (e.g., child safety seat). The monitoring device 204 may be positioned about the handle of the car seat in a plurality of orientations such that the camera 202 is facing the monitored passenger (e.g., child or infant). In one embodiment, the monitoring device may be positioned at the top of the carrying handle. In another embodiment, the monitoring device may be positioned on the left of right side of the carrying handle to ensure the grip of handle is not obstructed. As depicted in FIG. 2, the monitoring device 204 may include a camera 202 with a sliding cover 203, a battery life indicator 212, a camera link status indicator 206, and a pair of lights 208a, 208b (e.g., light emitting diodes (LEDs) for illuminating the camera's field of view during low lighting conditions). It should be noted that while the monitoring device 204 may include one or more of the elements listed, the monitoring device 204 is not limited to the listed features and may include additional elements not listed herein.

FIGS. 3A and 3B depict a retrofitted monitoring device 204 that is configured to be attached to a child safety seat or to a car seat handle in accordance with one embodiment of the present invention. In particular, FIG. 3A depicts the monitoring device 204 being retrofitted to a child safety seat, and FIG. 3B depicts the monitoring device 204 being unattached to a child safety seat or to a car seat handle. Such a feature is particularly advantageous in instances where an infant's car seat is positioned to face the rear of the motor vehicle.

In one embodiment, the monitoring device 204 may be positioned at the top of the carrying handle. In another embodiment, the monitoring device 204 may be positioned on the left of right side of the carrying handle to ensure the grip of handle is not obstructed. The monitoring device 304 may include a plurality of elements such as a camera 202, a battery life indicator 212, a camera link status indicator 206, a pair of lights 208*a*, 208*b*, and a lock knob 210. The lock knob 210 may be used to secure the retrofitted monitoring device 204 about an object, such as a car sear handle. In one embodiment, the lock knob 210 may have a twist and lock feature. In another embodiment, the lock knob 210 may snap into place. It should be noted that while the monitoring device 204 may include one or more of the elements listed, the monitoring device 204 is not limited to the listed features and may include additional elements not listed herein.

As illustrated in FIG. 4, in an alternative embodiment, the monitoring device 204 may be retrofitted to the headrest of a seat in a motor vehicle. In yet another embodiment illustrated in FIG. 5, the monitoring device 204 may be a DVD player with the ability to capture video images and retrofitted to a head rest of a seat in a motor vehicle. In a further embodiment, the monitoring device 204 may be a DVD player with the ability to capture video images and integrated in a head rest of a seat in a motor vehicle. Such features may be particularly advantageous in an embodiment when a child safety seat is positioned towards the front of a motor vehicle.

The monitor 106 may be any device (e.g., a mobile device or a car navigation device) capable of displaying images from one or more monitoring devices. Typically, the monitor 106 is capable of displaying video from a monitoring device in near-real time. By way of example, FIG. 6 depicts a monitor 306 that is a driver's mobile device configured to communicate directly or indirectly with a monitoring device. In some embodiments, the monitor 106 is or includes an interactive computer terminal that is configured to initiate, perform, complete, and/or facilitate one or more processes for monitoring a passenger. A monitor 106 could be or include any device that a driver may use to facilitate monitoring a passenger such as, but not limited to a computer (e.g., a personal computer, tablet computer, desktop computer, server, or laptop), a mobile device (e.g., a smartphone, cellular phone, personal digital assistant (PDA) device, MP3 device, or personal GPS device), a gaming device, and/or various combinations of the foregoing. In another embodiment, FIG. 7 depicts a monitor 306 that is integrated with a motor vehicle (e.g., an integrated navigation system, rear view monitor, or DVD player).

As depicted in FIG. 1, the monitor 106 typically includes a communication device 152, a processing device 154, a memory device 156, and a user interface 164. The processing device 154 is operatively coupled to the communication device 152, and the memory device 156. The communication device 152 generally includes a modem or other device (e.g., a built-in antenna) for communicating with other devices on the network 110. The user interface 164 may include a speaker for providing audio notifications. The user interface 164 typically includes a visual display 166 (e.g., a touch screen) that is configured to display from a monitoring device. In this regard, the monitor 106 is typically positioned in a motor vehicle so that an operator location (e.g., a driver seat or other place where an operator of the motor vehicle may be located) is within a field of view of the visual display 166. In other words, the monitor 106 is typically positioned so that the driver 102 can see the visual display 166 when operating the motor vehicle. For example, FIG. 8 depicts a monitor 306 being mounted on the dashboard of a motor vehicle, and FIG. 9A depicts a monitor 306 being mounted to the front window of a motor vehicle (e.g., using a mobile unit window mount 314 shown in FIG. 9A and FIG. 9B).

As further illustrated in FIG. 1, the monitor 106 typically includes computer-readable instructions 160 stored in the memory device 156, which in one embodiment includes the computer-readable instructions 160 of a monitor application 162. The processing device 154 (e.g., a processor) is typically configured to run the monitor application 162. In one embodiment illustrated in FIG. 6, the monitor application 162 allows the monitor 106 to be linked to the application server 108 to communicate, via a network 110, with the monitoring device 104. The monitor application 162 may also receive information from the application server 108.

As depicted in FIG. 6, the monitor may be a monitor 306 that includes include a plurality of elements such as a camera link status indicator 312, a temperature indicator 302, lighting option 304, a seat status indicator 310, and a carbon monoxide indicator 308. These various indicators may be disabled or enabled based upon user preferences. It should be noted that while the monitor may include one or more of the elements listed, the monitor is not limited to the listed features and may include additional elements not listed herein.

The monitor application 162 may be configured to detect the connection status between the monitor 106 and display an indicator of this status using the camera link status indicator 312.

In one embodiment, the monitor application 162 may be configured to display (e.g., via the carbon monoxide indicator 308) the carbon monoxide level detected by a monitoring device and provide a notification (e.g., a visual or audio notification) via the user interface of an unsafe detected level of carbon monoxide. In this regard, the carbon monoxide indicator 308 may include one or more lights (e.g., LEDs) that are illuminated one color (e.g., green) when carbon monoxide levels are safe and another color (e.g., red) when carbon monoxide levels are unsafe. In another embodiment, the monitor application 162 may be configured to display (e.g., via the temperature indicator 302) the motor vehicle temperature (e.g., internal temperature) detected by a monitoring device and provide a notification (e.g., a visual or audio notification) via the user interface of an unsafe detected temperature. In this regard, the temperature indicator 302 may include one or more lights (e.g., LEDs) that are illuminated one color (e.g., green) when the temperature is safe and another color (e.g., red) when the temperature is unsafe. The temperature indicator 302 may also be used to display the temperature outside of the motor vehicle (e.g., from an exterior temperature sensor in communication with the monitor 106).

In yet another embodiment, the monitor application 162 may be configured to display (e.g., via the user interface) information from a seat sensing pad positioned in a child safety seat. For example, the temperature of a child in the child safety seat may be displayed via the temperature indicator 308.

In a further embodiment, the monitor application 162 may be configured to display (e.g., via the user interface) information from a seat status sensor attached to a child safety seat. For example, an indication of whether a child is secured in the child safety seat may be displayed via the seat status indicator 310. In this regard, the seat status indicator 310 may include one or more lights (e.g., LEDs) that are illuminated one color (e.g., green) when the child safety seat is secured and another color (e.g., red) when the child safety seat is unsecured.

The lighting option 304 may be used to control the interior lights of a motor vehicle. In another embodiment, the lighting option 304 may control lights integrated with the monitor 106, itself. In yet another embodiment, the lighting option 304 may control a monitoring device's lights that are used to illuminate a camera's field of view during low lighting conditions. The lighting option 304 may be a touch screen option such that the driver 102 is able to touch the monitor 106 to control the lighting options in the motor vehicle. In an alternative embodiment, the lighting option 304 may be a button that is integrated with the monitor 106 such that the driver 102 may press the button to control the lighting options within the motor vehicle. In yet another embodiment, the lighting option 304 may serve as an indicator such that the driver 102 may use voice commands to control the lighting options in the motor vehicle and the lighting option 304 may indicate whether the lights have been turned on and/or off.

In one embodiment, the monitor application 162 is configured to analyze images received from a monitoring device to detect changes in a passenger's color and provide a notification (e.g., an audio or visual notification) via the user interface (e.g., via an audio notification device) of a detected change (e.g., a significant change) to a passenger's color.

In one embodiment, the monitor 106 may have auto adjusting viewing technology such that a quality image is provided in all lighting conditions (e.g., in low lighting conditions and in extreme sun light).

In some embodiments, the monitor may be in communication with a plurality of monitoring devices. Accordingly, the monitor 106 may have split viewing options such that two near-real-time image feeds (e.g., video feeds) may be displayed on the monitor simultaneously. Alternatively, the monitor 106 may toggle between displaying images from a plurality of monitoring devices or from a plurality of image capturing devices on a single monitoring device. For example, two near-real-time video feeds may be alternately displayed for five second intervals. The monitor 106 may also have Twin-View/Trifecta technology (hereinafter, "TVT") to allow for toggling in between two or more image feeds during the monitoring process. In one embodiment, the monitor application 162 is configured to determine if there is a passenger issue associated with one monitoring device or image capturing device and continuously displaying images (e.g., on the visual display 166) from the monitoring device or image capturing device associated with the passenger issue during the duration of the passenger issue (e.g., until the passenger issue is resolved). For example, the monitor application 162 may determine that a sensing seat pad positioned in a child safety that is monitored by a first monitoring device has detected moisture, which may be indicative of a wet diaper. The monitor application 162 would then continuously display images from the first monitoring device on the visual display 166 until the sensing seat pad no longer detects moisture.

As noted, the monitor 106 may be a mobile device. In such an embodiment, telephone and/or text-messaging functionality of the mobile device's communications system may be disabled when the mobile device is being utilized as a monitor 106. In one embodiment, telephone and/or text-messaging functionality of the mobile device's communications system may be disabled only when motion is detected in the motor vehicle (e.g., with a GPS or accelerometer in the mobile device). In another embodiment, telephone and/or text-messaging functionality of the mobile device's communications system may be disabled only when a predetermined amount of motion is detected in the motor vehicle, such as if the motor vehicle is exceeding a particular speed (e.g., at least 5 miles per hour). In one embodiment, an auto response message may be sent to individuals attempting to communicate with the mobile device while it is being utilized as a monitor. The message may inform an individual that the driver 102 is currently operating a motor vehicle with precious cargo such as an infant, child, passenger, and/or the like. In another embodiment, once the monitor application is closed such that the mobile device is no longer being utilized as a monitor 106, the driver 102 may be instantly notified of all text based communication.

Now referring to FIG. 10, a view of a mobile application interface is provided, according to an embodiment of the claimed invention. In one embodiment the system may also include a web based application such that a real-time video feed may be provided on the web. In one embodiment, the real time video feed may be provided via an IP address.

While the foregoing disclosure discusses illustrative embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any embodiment may be utilized with all or a portion of any other embodiment, unless stated otherwise.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

The invention claimed is:
1. A system for passenger monitoring, comprising:
a first monitoring device positioned in a motor vehicle, the first monitoring device comprising a first camera having a field of view directed towards a first passenger location in the motor vehicle;
a second monitoring device positioned in the motor vehicle, the second monitoring device comprising a camera having a field of view directed towards a second passenger location in the motor vehicle, the second monitoring device being in communication with a mobile device;
the mobile device comprising a user interface, a communications system, a motion sensor, and a processor in communication with the user interface, the communications system, the motion sensor, and the first monitoring device, the user interface comprising a visual display, the processor being configured to operate a passenger monitoring application, the passenger monitoring application being configured to:
receive images from the first camera and display the images on the visual display in near real time;
detect motion using the motion sensor;
in response to receiving images from the first camera and displaying the images on the visual display and a predetermined amount of detected motion, disable any telephone and text-messaging functionality of the communications system;

receive images from the second monitoring device's camera and display the images on the visual display in near real time;

toggle between displaying images from the first monitoring device on the visual display and images from the second monitoring device on the visual display;

determine that there is a passenger issue associated with the first monitoring device or the second monitoring device; and continuously display images from the monitoring device associated with the passenger issue in response to determining that there is a passenger issue associated with the first monitoring device or second monitoring device and disable the toggle between displaying images from the first monitoring device on the visual display and images from the second monitoring device on the visual display.

2. The system for passenger monitoring according to claim 1, comprising a seat sensing pad positioned in a child safety seat, the seat sensing pad being configured to detect (i) moisture in the child safety seat, (ii) the temperature of a passenger located in the child safety seat, and/or (iii) the heart rate of a passenger located in the child safety seat, wherein the seat sensing pad is in communication with the mobile device, and wherein the passenger monitoring application is configured to display information from the seat sensing pad on the visual display.

3. The system for passenger monitoring according to claim 1, wherein the passenger monitoring application is configured to (i) analyze the images received from the first camera to detect changes to a passenger's color and (ii) provide a notification via the user interface of a detected change to a passenger's color.

4. The system for passenger monitoring according to claim 1, wherein the passenger monitoring application is configured to (i) detect a status of the connection between the first monitoring device and the mobile device and (ii) display an indicator of the status of the connection between the first monitoring device and the mobile device on the visual display.

5. The system for passenger monitoring according to claim 1, wherein the passenger monitoring application is configured to:

receive a communication from a sender; and automatically transmit an auto response message to the sender attempting to communicate with the mobile device in response to disabling any telephone and text-messaging functionality of the communications system and receiving the communication from the sender.

6. The system for passenger monitoring according to claim 5, wherein the auto response message is configured to inform the sender attempting to communicate with the mobile device that a driver is currently operating a motor vehicle and transporting a child or an infant.

7. The system for passenger monitoring according to claim 1, wherein the passenger monitoring application is configured to:

disable passenger monitoring; and enable the telephone and text-messaging functionality of the communications system in response to disabling passenger monitoring.

8. The system for passenger monitoring according to claim 1, wherein determining that there is a passenger issue comprises determining that a seat sensing pad associated with the first monitoring device or the second monitoring device has detected moisture.

9. The system for passenger monitoring according to claim 1, wherein disabling the toggle between displaying images from the first monitoring device on the visual display and images from the second monitoring device on the visual display comprises disabling the toggle between displaying images from the first monitoring device on the visual display and images from the second monitoring device on the visual display until the passenger issue is resolved.

10. A system for passenger monitoring, comprising:

a first monitoring device positioned in a motor vehicle, the first monitoring device comprising a first camera having a field of view directed towards a first passenger location in the motor vehicle and a second camera having a field of view directed towards a second passenger location in the motor vehicle;

a mobile device comprising a user interface, a communications system, a motion sensor, and a processor in communication with the user interface, the communications system, the motion sensor, and the first monitoring device, the user interface comprising a visual display, the processor being configured to operate a passenger monitoring application, the passenger monitoring application being configured to:

receive images from the first camera and display the images on the visual display in near real time;

detect motion using the motion sensor;

in response to receiving images from the first camera and displaying the images on the visual display and a predetermined amount of detected motion, disable any telephone and text-messaging functionality of the communications system;

receive images from the second camera and display the images on the visual display in near real time;

toggle between displaying images from the first camera on the visual display and images from the second camera on the visual display;

determine that there is a passenger issue associated with the first camera or the second camera; and continuously display images from the camera associated with the passenger issue in response to determining that there is a passenger issue associated with the first camera or the second camera and disable the toggle between displaying images from the first camera on the visual display and images from the second camera on the visual display.

11. The system for passenger monitoring according to claim 10, comprising a seat sensing pad positioned in a child safety seat, the seat sensing pad being configured to detect (i) moisture in the child safety seat, (ii) the temperature of a passenger located in the child safety seat, and/or (iii) the heart rate of a passenger located in the child safety seat, wherein the seat sensing pad is in communication with the mobile device, and wherein the passenger monitoring application is configured to display information from the seat sensing pad on the visual display.

12. The system for passenger monitoring according to claim 10, wherein the passenger monitoring application is configured to (i) analyze the images received from the first camera to detect changes to a passenger's color and (ii) provide a notification via the user interface of a detected change to a passenger's color.

13. The system for passenger monitoring according to claim 10, wherein the passenger monitoring application is configured to (i) detect a status of the connection between the first monitoring device and the mobile device and (ii)

display an indicator of the status of the connection between the first monitoring device and the mobile device on the visual display.

14. The system for passenger monitoring according to claim 10, wherein the passenger monitoring application is configured to:
  receive a communication from a sender; and
  automatically transmit an auto response message to the sender attempting to communicate with the mobile device in response to disabling any telephone and text-messaging functionality of the communications system and receiving the communication from the sender.

15. The system for passenger monitoring according to claim 14, wherein the auto response message is configured to inform the sender attempting to communicate with the mobile device that a driver is currently operating a motor vehicle and transporting a child or an infant.

16. The system for passenger monitoring according to claim 10, wherein the passenger monitoring application is configured to:
  disable passenger monitoring; and
  enable the telephone and text-messaging functionality of the communications system in response to disabling passenger monitoring.

17. The system for passenger monitoring according to claim 10, wherein determining that there is a passenger issue comprises determining that a seat sensing pad associated with the first camera or the second camera has detected moisture.

18. The system for passenger monitoring according to claim 10, wherein disabling the toggle between displaying images from the first camera on the visual display and images from the second camera on the visual display comprises disabling the toggle between displaying images from the first camera on the visual display and images from the second camera on the visual display until the passenger issue is resolved.

* * * * *